US00PP30294P2

(12) United States Plant Patent
Nishikawa

(10) Patent No.: US PP30,294 P2
(45) Date of Patent: Mar. 12, 2019

(54) ***DELOSPERMA* PLANT NAMED 'DE18-152'**

(50) Latin Name: *Delosperma cooperi*
Varietal Denomination: DE18-152

(71) Applicant: Koichiro Nishikawa, Katuta-Gun (JP)

(72) Inventor: Koichiro Nishikawa, Katuta-Gun (JP)

( * ) Notice: Subject to any disclaimer, the term of this patent is extended or adjusted under 35 U.S.C. 154(b) by 0 days.

(21) Appl. No.: 15/732,271

(22) Filed: Oct. 17, 2017

(51) Int. Cl.
*A01H 5/02* (2018.01)

(52) U.S. Cl.
USPC ..... Plt./422

(58) Field of Classification Search
USPC ..... Plt./263.1, 422
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Delosperma* plant, 'DE18-152', characterized by its compact and horizontal plant habit, its very floriferous and long blooming habit, its very floriferous and long blooming flowering habit, its high heat tolerance, and its flowers that are pure orange with pink centers and yellow anthers with petals with a very shiny surface.

2 Drawing Sheets

Botanical classification: *Delosperma cooperi.*
Variety denomination: 'DE18-152'.

BACKGROUND OF THE INVENTION

The present invention relates to a new and distinct cultivar of *Delosperma* plant, botanically known as *Delosperma cooperi* 'DE18-152' and will be referred to hereinafter by its cultivar name, 'DE18-152'. The new cultivar of *Delosperma* is an herbaceous perennial grown for container and landscape use.

The new cultivar in Ichinimiya-City, Aichi-Pref, Japan. The overall purpose of the breeding program was to develop new cultivars of *Delosperma* plants with low-growing and well-spreading growth habits combined with long flowering periods and a unique range of flower colors.

'DE18-152' arose from a crosses made by the Inventor between unnamed and unpatented proprietary plants of *Delosperma cooperi* from his breeding program. Seeds were pooled from the crosses and therefore the exact parentage is unknown. 'DE18-152' was selected in 2015 as a single unique plant amongst the resulting seedlings.

Asexual propagation of the new cultivar was first accomplished by softwood cuttings in 2015 by the Inventor in Ichinimiya-City, Aichi-Pref, Japan. Propagation by softwood cuttings has shown that the unique features of the new cultivar are stable and reproduced true to type in successive generations.

SUMMARY OF THE INVENTION

The following traits have been repeatedly observed and are determined to be the characteristics of the new cultivar. These attributes in combination distinguish 'DE18-152' as a unique cultivar of *Delosperma.*

1. 'DE18-152' exhibits a compact and horizontal plant habit
2. 'DE18-152' exhibits a floriferous and long blooming habit.
3. 'DE18-152' exhibits high heat tolerance.

4. 'DE18-152' exhibits flowers that are pure orange with pink centers and yellow anthers.
5. 'DE18-152' exhibits flower petals with a very shiny surface.

'DE18-152' can be most closely compared to *Delosperma cooperi* cultivars 'DSAA13-1' (U.S. Plant Pat. No. 27,014) and 'WOWDOY3' (U.S. Plant Pat. No. 25,600). 'DSAA13-1' differs from 'DE18-152' in having flower petals that are red-orange in color. 'WOWDOY3' differs from 'DE18-152' in having flower petals that are orange near the petals tips and change to yellow towards the base.

BRIEF DESCRIPTION OF THE DRAWINGS

The accompanying colored photographs illustrate the overall appearance and distinct characteristics of the new *Delosperma*. The plant in the photograph is 3 months in age as grown in a 1-liter container grown in an unheated greenhouse in Noordwijkerhout, The Netherlands.

The photograph in FIG. 1 provides a side view of 'DE18-152' in bloom.

Figure 1:
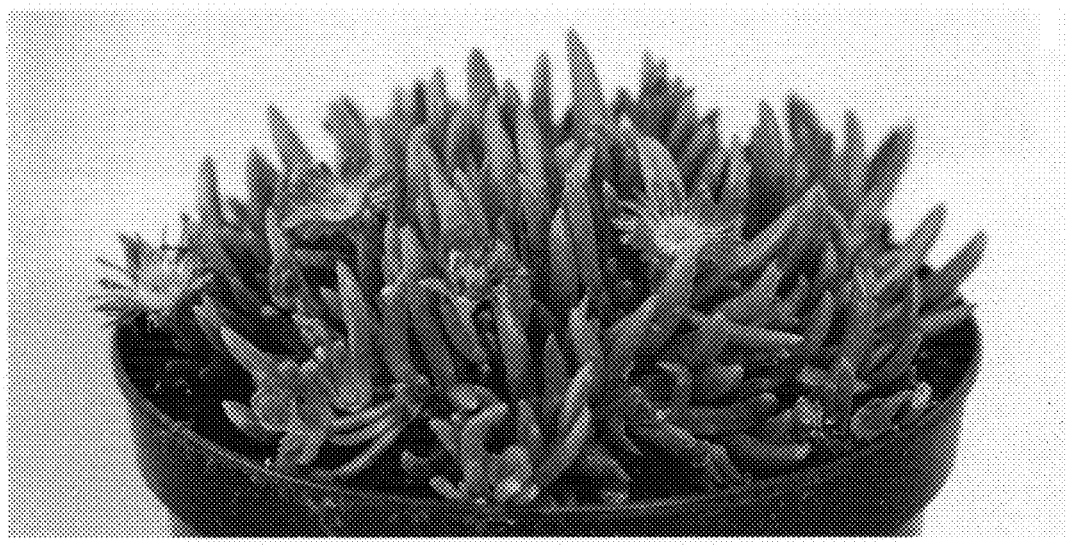
Figure 2:
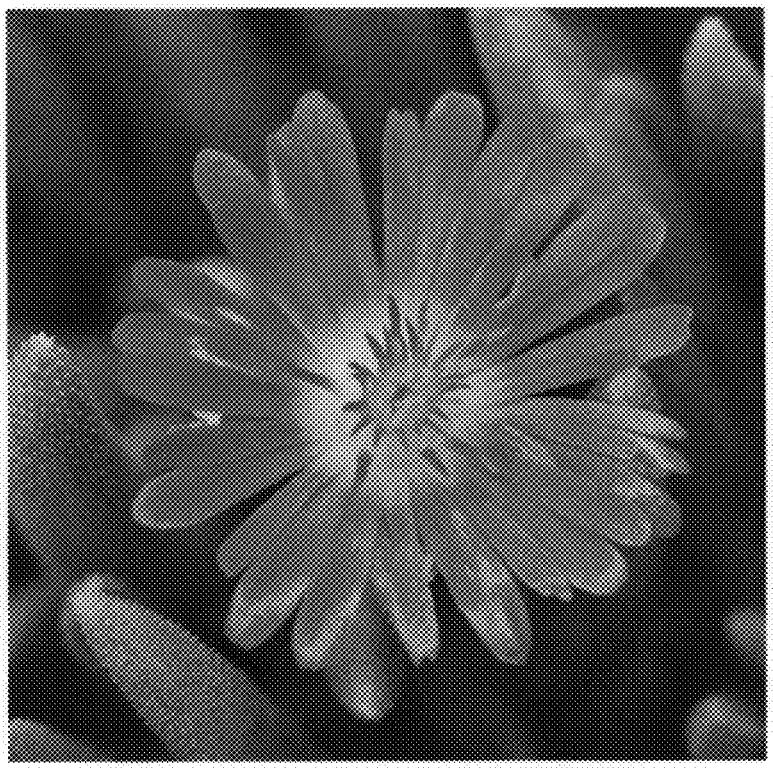

The photograph in FIG. 2 provides a close-up view of a flower of 'DE18-152'.

Figure 3:
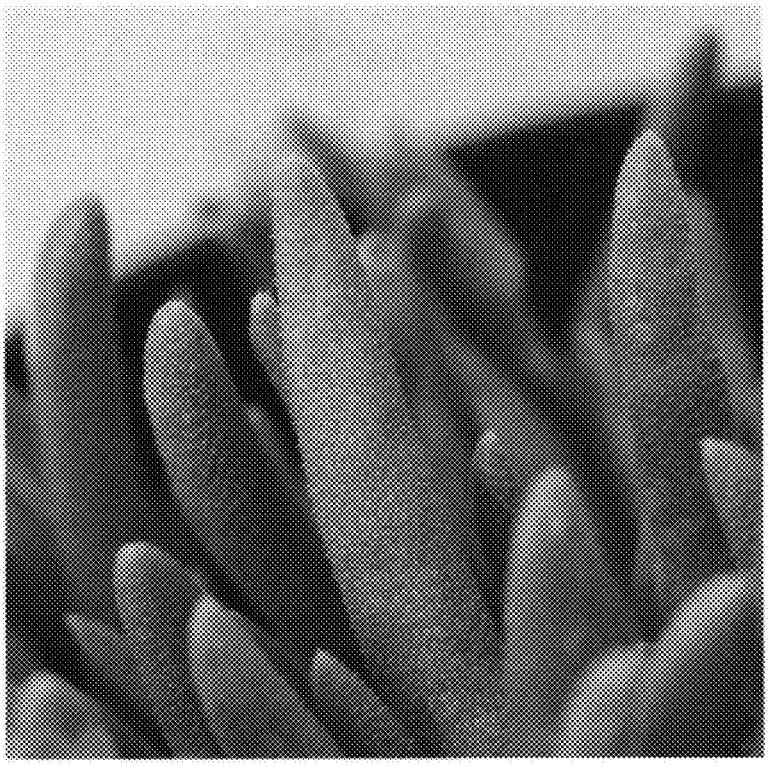

The photograph in FIG. 3 provides a close-up view of the foliage of 'DE18-152'.

The colors in the photographs may differ slightly from the color values cited in the detailed botanical description, which accurately describe the colors of the new *Delosperma.*

DETAILED BOTANICAL DESCRIPTION

The following is a detailed description of three month-old plants of the new cultivar as grown in 1-liter containers in an unheated greenhouse in Noordwijkerhout, The Netherlands. The phenotype of the new cultivar may vary with variations in environmental, climatic, and cultural conditions, as it has not been tested under all possible environmental conditions. The color determination is in accordance with The 2015 Royal Horticultural Society Colour Chart of The Royal Horticultural Society, London, England, except where general color terms of ordinary dictionary significance are used.

General description:

*Blooming period*.—Late spring to late summer in Noordwijkerhout, The Netherlands.

*Plant type*.—Herbaceous perennial.

*Plant habit*.—Compact, well-spreading, horizontal.

*Height and spread*.—Reaches about 5.3 cm in height and 14.3 cm in diameter as grown in a 1-liter container.

*Cold hardiness*.—Observed to be hardy in U.S.D.A. Zones 7 to 12.

*Diseases and pests*.—No susceptibility to resistance to diseases or pests has been observed.

*Root description*.—Fibrous roots, 162D in color.

*Propagation*.—Softwood cuttings.

*Growth habit*.—Moderately vigorous.

*Root development*.—Roots initiate and fill a 104-cell plug in 3 weeks and the planted plugs fully develop in 9-cm container within 6 weeks.

Stem description:

*Shape*.—Round.

*Stem color*.—Young stems; 146B, mature stems; 145C, strongly tinged with N170D.

*Stem size*.—Lateral branches; an average of 2.8 cm in length and 2 mm in diameter.

*Internode length*.—An average of 1 cm.

*Stem texture*.—Succulent.

*Stem surface*.—Slightly glossy, sparsely to moderately pubescent with very short glandular hairs; an average of 0.2 mm in length, very minute in size, closest to NN155D in color.

*Stem aspect*.—Held in an average angle of 90°.

*Stem strength*.—Strong.

*Branching habit*.—An average of 15 primary branches and 30 lateral branches per plant.

Foliage description:

*Leaf shape*.—Ligulate, triangular in diameter.

*Leaf substance*.—Succulent.

*Leaf division*.—Simple.

*Leaf base*.—Cuneate.

*Leaf apex*.—Acute.

*Leaf venation*.—No veins visible.

*Leaf margins*.—Entire.

*Leaf aspect*.—Slightly curved.

*Leaf arrangement*.—Opposite.

*Leaf surface*.—Both surfaces smooth, moderately glossy and densely covered with very short glandular hairs, average of 0.2 mm, very hard to measure color due to small size, closest to 157D in color.

*Leaf color*.—Upper surface; 138A, lower surface 137B.

*Leaf size*.—About 4.2 cm in length and 5 mm in width.

*Leaf quantity*.—Average of 6 (3 pairs) per lateral branch.

*Leaf attachment*.—Sessile.

Inflorescence description:

*Inflorescence type*.—Flowers solitary.

*Flower number*.—An average of 4 flowers and 41 buds per plant.

*Flower fragrance*.—Faint, sweet and pleasant.

*Flower aspect*.—Upright to slightly outward.

*Flower longevity*.—Average of 10 days.

*Flower type*.—Single, rotate.

*Flower size*.—Average of 2.3 cm in height and diameter and 8 mm in depth.

*Flower buds*.—Ovate in shape, an average of 8 mm in length and 4.5 mm in diameter, 138A in color, base 144B in color, surface is slightly glossy and densely covered with very short glandular hairs an average of 0.2 mm in length, 157D in color.

*Calyx*.—Rotate in shape, average of 7 mm in depth and 1.4 cm in diameter.

*Sepals*.—5, rotate, narrowly ovate in shape, margin entire, an average of 7 mm in length and 2 mm in width, acute apex, broadly cuneate base, color; opening and fully open flowers upper and lower surface; 138B.

*Petals*.—An average of 50 per flower, rotate, narrowly oblanceolate in shape, upper and lower surface is smooth, glossy, glabrous and velvety, margin entire, apex obtuse, base narrowly cuneate, an average of 1 cm in length and 1.75 mm in width, color: opening flowers upper and lower surface; 34A, fading to 72C at the base, fully opened flower upper surface; N30A, fading to 72C at the base, fully opened flower lower surface; 33A, fading to 72C at the base.

*Petaloids*.—None present.

*Peduncle*.—None present.

*Pedicel*.—Average of 1.1 cm in length and 1.5 mm in diameter, held straight on top of lateral branch at 0° to 30°, 145A in color, surface slightly glossy, moderately strong in strength, 145A in color, surface is slightly glossy and densely covered with very short glandular hairs, average of 0.2 mm in length and 157D in color.

Reproductive organs:

*Pistils*.—Average of 5, style and stigma; no separate stigma and style visible (not distinguishable) triangular in shape, are an average of 2 mm in length, 0.75 mm in diameter and N144B in color, ovary; 144A in color.

*Stamens*.—Average 50, anthers; dorsifixed and ovate in shape, an average of 0.5 mm in length and 0.2 mm in width, 13A in color, filaments; 2 mm in length and 157D in color, pollen; moderate in quantity and 12B in color.

*Fruit/seed*.—Fruit and seed production has not been observed to date.

It is claimed:

1. A new and distinct variety of *Delosperma* plant named 'DE18-152' as described and illustrated herein.

* * * * *